United States Patent
Yin et al.

(10) Patent No.: US 7,001,896 B2
(45) Date of Patent: Feb. 21, 2006

(54) COMPOSITIONS FOR TREATING DIABETES

(75) Inventors: Weidong Yin, Hengyang (CN); Kazuhiko Tsutsumi, Tokushima (JP)

(73) Assignees: Yin Weidong, Hunan (CN); Otsuka Pharmaceutical Factory, Inc., Tokushima (JP)

(*) Notice: Subject to any disclaimer, the term of this patent is extended or adjusted under 35 U.S.C. 154(b) by 321 days.

(21) Appl. No.: 10/381,731

(22) PCT Filed: Sep. 28, 2001

(86) PCT No.: PCT/JP01/08497

§ 371 (c)(1),
(2), (4) Date: Mar. 26, 2003

(87) PCT Pub. No.: WO02/28398

PCT Pub. Date: Apr. 11, 2002

(65) Prior Publication Data

US 2004/0014728 A1   Jan. 22, 2004

(30) Foreign Application Priority Data

Sep. 29, 2000 (JP) ................................ 2000-06741

(51) Int. Cl.
*A61K 31/66* (2006.01)
*A61K 31/685* (2006.01)
(52) U.S. Cl. ........................... 514/119; 514/75; 514/76
(58) Field of Classification Search ................ 514/119, 514/75, 76
See application file for complete search history.

(56) References Cited

FOREIGN PATENT DOCUMENTS

| EP | 0 402 033 | 7/1993 |
| JP | 5-953 | 1/1993 |
| JP | 5-953 A | 1/1993 |
| JP | 5-170653 | 7/1993 |
| JP | 5-170653 A | 7/1993 |

OTHER PUBLICATIONS

International Search Report for PCT/JP01/08497 dated Dec. 25, 2001.

*Primary Examiner*—Sreeni Padmanabhan
*Assistant Examiner*—Jennifer Kim
(74) *Attorney, Agent, or Firm*—Sughrue Mion, PLLC

(57) ABSTRACT

The present invention provides a pharmaceutical composition for treating diabetes containing 4-diethoxyphosphinoyl-methyl-N-(4-bromo-2-cyanophenyl)benzamide, particularly a pharmaceutical composition for treating diabetes that exhibits excellent effects for treating type II diabetes and the prevention of diabetic complications.

4 Claims, No Drawings

COMPOSITIONS FOR TREATING DIABETES

CROSS-REFERENCE TO RELATED APPLICATION

This application is a 371 of PCT/JP01/08497, filed Sep. 28, 2001. The disclosure of which is incorporated herein by reference.

TECHNICAL FIELD

The present invention relates to a composition for treating diabetes and a method for treating diabetes.

BACKGROUND OF THE INVENTION

Recent years have seen an increasing number of diabetic patients and patients suffering from the complications thereof, and an increasing incidence of diabetes in young people resulting from improvements in the standard of living, changes toward European and American styles of eating, a growing tendency toward insufficient exercise, and the like.

Generally, diabetes mellitus includes insulin-dependent (type I) and non-insulin-dependent (type II) diabetes, and 90% or more of all diabetic patients suffer from the latter.

For treating diabetes, in addition to therapeutic exercise and dietary management, insulin injections are used for type I diabetes and oral drugs other than insulin are mainly used for type II diabetes. Oral drugs known to be useful for treating type II diabetes include insulin secretion stimulators such as sulfonyl ureas (SUs), and anaerobic glycolysis promoters such as biguinides.

The primary goal of treating diabetes is to prevent the development of diabetic complications. However, according to clinical reports concerning the prognoses of patients administered with an insulin secretion stimulator and an anaerobic glycolysis promoter over a long period of time, it is clear that the effect of preventing the development of diabetic complications is not always satisfactory.

Further, it is reported that the administration of various insulin secretion stimulators may cause severe, prolonged hypoglycemia, and, particularly, the long-term administration thereof may pose an increased burden on the pancreas, causing a transition of the pathological state to type I diabetes. It is also reported that the administration of an insulin secretion stimulator may cause chronic hypersecretion of insulin, and that this chronic hypersecretion of insulin, as a result, leads to the development of complications.

As for the anaerobic glycolysis promoters, serious side effects, such as severe lactic acidosis, hypoglycemia and the like have been reported (see, e.g., Rinsho Seijinbyo (The Journal of Adult Diseases), 6(6), 859–865 (1976)).

DISCLOSURE OF THE INVENTION

An object of the present invention is to provide a novel antidiabetic agent that overcomes the drawbacks of the prior art, has excellent pharmacological activity, particularly for lowering the blood glucose level, and is highly safe, and a method for treating diabetes using the agent.

As a result of intensive investigations, the inventors found that a specific carboxylic amide derivative, i.e., 4-diethoxyphosphinoylmethyl-N-(4-bromo-2-cyanophenyl)benzamide, is effective as an active ingredient for an antidiabetic agent that achieves the above objectives. The present invention was accomplished based on this finding.

The present invention provides a pharmaceutical composition for treating diabetes comprising an effective amount of 4-diethoxyphosphinoylmethyl-N-(4-bromo-2-cyanophenyl)benzamide and a pharmaceutically acceptable carrier.

In particular, the present invention provides a pharmaceutical composition for treating diabetes that can be used for treating type II diabetes, and a pharmaceutical composition for treating diabetes that can be used as a blood glucose lowering agent.

The present invention also provides a method for treating diabetes comprising administering to a diabetic patient a therapeutically effective amount of 4-diethoxyphosphinoyl-methyl-N-(4-bromo-2-cyanophenyl)-benzamide.

Specifically, the present invention provides a method for treating type II diabetes, and a method for treating diabetes employing the blood glucose lowering activity of the composition.

Further, the present invention provides the use of 4-diethoxyphosphinoylmethyl-N-(4-bromo-2-cyano-phenyl)benzamide for preparing a pharmaceutical composition for treating diabetes, particularly the use of the compound for preparing a pharmaceutical composition for treating type II diabetes, and the use of the compound for preparing an pharmaceutical composition for treating diabetes having a blood glucose lowering activity.

In the pharmaceutical composition of the present invention for treating diabetes, the 4-diethoxyphosphinoylmethyl-N-(4-bromo-2-cyanophenyl)benzamide to be used as an active ingredient is represented by the following formula:

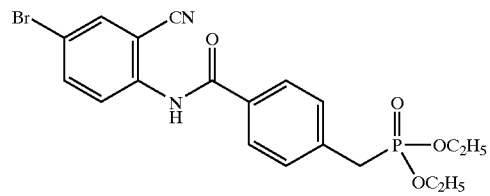

The inventors have proposed the above compound as an active ingredient for anti-inflammatory compositions (see U.S. Pat. No. 4,822,780), and developed it as an active ingredient for antihyperlipidemic compositions (see U.S. Pat. No. 5,081,112 and Japanese Unexamined Patent Publication No. 68592/1991).

In the above publications, however, there is no description of the effectiveness of the compound in treating diabetes. Naturally, there is also no suggestion of the blood glucose lowering activity thereof.

The compound can be produced according to the method disclosed in the publications, for example, by reacting a carboxylic halide such as 4-diethoxyphosphinoylmethylbenzoyl chloride with 4-bromo-2-cyanophenylamine.

The compound exhibits excellent effects particularly for treating type II diabetes and the prevention of diabetic complications. In addition, it has a remarkable property in that it does not cause serious side effects as those that are encountered with conventional antidiabetic agents of this kind.

It is important that the pharmaceutical composition of the invention for treating diabetes contains as an active ingredient the compound described above. The pharmaceutical composition can generally be prepared in various forms according to the administration method employing pharmaceutically acceptable carriers that are commonly used in this field.

Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination of two or more species according to the form of the pharmaceutical preparation. The resulting preparation may incorporate, if necessary, one or more solubilizing agent, buffers, preservatives, colorants, perfumes, flavorings and the like that are widely used in the field of pharmaceutical preparation.

The form and administration route for the pharmaceutical composition of the invention are not limited and can be suitably selected. Examples of the form are oral forms such as tablets, capsules, granules, pills, syrups, solutions, emulsions, suspensions and the like, and parenteral forms such as injections (e.g., subcutaneous, intravenous, intramuscular and intraperitoneal injections) and the like. The above oral forms are administered orally. The parenteral forms, such as injections, may be administered intravenously either singly or in combination with a conventional replenisher containing glucose, amino acid and/or the like, or may be singly administered intramuscularly, intracutaneously, subcutaneously or intraperitoneally.

The pharmaceutical composition of the invention for treating diabetes may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The proportion of the active ingredient to be contained in the pharmaceutical composition of the invention for treating diabetes can be suitably selected from a wide range. Usually, it is preferable to select from a range in which the pharmaceutical composition contains 1 to 70 wt. % of the active ingredient.

The amount administered for the pharmaceutical composition of the invention for treating diabetes is not limited and can be suitably selected according to the form of the pharmaceutical composition; administration route; and age, body weight, and degree of the disease of the patient; etc. It is usually preferable to include the active ingredient in an oral form of the pharmaceutical composition in an amount of about 0.05 to about 80 mg, preferably about 0.1 to about 50 mg, per kilogram of adult body weight per day. This amount, however, can be suitably increased or decreased as necessary.

BEST MODE FOR CARRYING OUT THE INVENTION

In order to illustrate the present invention in more detail, examples of the pharmaceutical composition of the invention for treating diabetes are given below as formulation examples.

FORMULATION EXAMPLE 1

Preparation of Tablets

Tablets (1,000 tablets) each containing 250 mg of 4-diethoxyphosphinoylmethyl-N-(4-bromo-2-cyanophenyl)benzamide (hereinafter referred to as "Compound A") as an active ingredient were prepared according to the following formulation.

| Ingredient | Amount (g) |
| --- | --- |
| Compound A | 250 |
| Lactose (Japanese Pharmacopeia) | 33.3 |
| Corn starch (Japanese Pharmacopeia) | 16.4 |
| Carboxymethylcellulose calcium (Japanese Pharmacopeia) | 12.8 |
| Methylcellulose (Japanese Pharmacopeia) | 6.0 |
| Magnesium stearate (Japanese Pharmacopeia) | 1.5 |
| Total | 320 |

Using the above formulation, Compound A, lactose, corn starch and carboxymethylcellulose calcium were sufficiently mixed, the mixture was granulated using a methylcellulose aqueous solution, the granules were passed through a 24-mesh sieve and mixed with magnesium stearate, and the resulting mixture was pressed to form tablets.

FORMULATION EXAMPLE 2

Preparation of Capsules

Hard gelatin capsules (1,000 capsules) each containing 250 mg of Compound A were prepared according to the following formulation.

| Ingredient | Amount (g) |
| --- | --- |
| Compound A | 250 |
| Crystalline cellulose (Japanese Pharmacopeia) | 30 |
| Corn starch (Japanese Pharmacopeia) | 17 |
| Talc (Japanese Pharmacopeia) | 2 |
| Magnesium stearate (Japanese Pharmacopeia) | 1 |
| Total | 300 |

Using the above formulation, each ingredient was powdered and they were thoroughly mixed to give a uniform mixture. The desired capsules were then prepared by filling gelatin capsules having an appropriate size for oral administration with the mixture.

FORMULATION EXAMPLE 3

Preparation of Granules

Granules (1,000 g) containing 500 mg of Compound A per gram were prepared according to the following formulation.

| Ingredient | Amount (g) |
| --- | --- |
| Compound A | 500 |
| Corn starch (Japanese Pharmacopeia) | 250 |
| Lactose (Japanese Pharmacopeia) | 100 |
| Crystalline cellulose (Japanese Pharmacopeia) | 100 |
| Carboxymethylcellulose calcium (Japanese Pharmacopeia) | 40 |
| Hydroxypropylcellulose (Japanese Pharmacopeia) | 10 |
| Total | 1000 |

Using the above formulation, Compound A, corn starch, lactose, crystalline cellulose and carboxymethylcellulose calcium were mixed, a hydroxypropylcellulose aqueous solution was added to the mixture, the resulting mixture was kneaded and granulated by an extrusion granulator, and the granules were dried at a temperature of 50° C. for 2 hours to give the desired granular composition.

Given below is a pharmacological test example conducted for the active ingredient of the pharmaceutical composition of the invention for treating diabetes.

PHARMACOLOGICAL TEST EXAMPLE 1

In this test, New Zealand white rabbits each weighing about 2 kg were divided into three groups, i.e., Group 1 consisting of 5 rabbits, Group 2 consisting of 6 rabbits, and Group 3 consisting of 6 rabbits.

The Group 1 rabbits were fed on an ordinary feed (Standard laboratory chow for rabbits, product of Shanghai Shengwang Experimental Animal Ranch (P.R. China)) (Normal Group).

The Group 2 rabbits were given for 4 weeks a high-fat, high-sugar feed prepared by adding 10% lard and 37% sucrose to the above-described standard laboratory chow. After confirming increases in blood glucose level, these rabbits were fed a high-fat, high-sugar feed as described above but containing 1% of the active ingredient (Compound A) of the pharmaceutical composition of the invention for treating diabetes (Experimental Group).

The Group 3 rabbits were fed the high-fat, high-sugar feed prepared by adding 10% lard and 37% sucrose to the standard laboratory chow described above (Control Group).

The rabbits of each group were allowed to eat the respective feeds ad libitum. In all groups, the amount of feed given was 35 g/kg/day per rabbit. The test period (period of feeding) was 24 weeks.

At the beginning of the test (0 week) and 4 weeks, 8 weeks, 12 weeks, 16 weeks, 20 weeks and 24 weeks later, the rabbits of each group fasted overnight, and blood samples were then collected from the auricular artery and assayed to measure the serum glucose level (mg/dl) using a commercially available glucose determination kit for enzymatic assaying (Glucose determination kit (Glucose oxidase-peroxidase method), product of Shanghai Rongsheng Biotech Inc. (P.R China).

The results (mean±S.D.) obtained are shown in Table 1 below.

TABLE 1

| Test group | Group 1 (n = 5) | Group 2 (n = 6) | Group 3 (n = 6) |
| --- | --- | --- | --- |
| 0 week later | 76.0 ± 12.9 | 68.8 ± 10.3 | 71.7 ± 11.3 |
| 4 weeks later | 65.2 ± 8.7 | 133.3 ± 28.6 | 108.0 ± 20.5 |
| 8 weeks later | 68.4 ± 4.6 | 124.7 ± 29.2 | 113.3 ± 13.2 |
| 12 weeks later | 53.6 ± 9.2 | 84.7 ± 19.5 | 119.5 ± 8.1 |
| 16 weeks later | 56.8 ± 11.5 | 85.3 ± 12.8 | 123.0 ± 7.7 |
| 20 weeks later | 57.6 ± 11.5 | 90.0 ± 15.7 | 125.5 ± 6.0 |
| 24 weeks later | 52.0 ± 6.3 | 73.6 ± 6.1 | 125.0 ± 5.8 |

The results shown in Table 1 clearly reveal that:

(1) the group (Group 3, Control Group) that was given the high-fat, high-sugar feed not containing the active ingredient of the pharmaceutical composition of the invention for treating diabetes (Compound A) showed a continuous increase in blood glucose level during the test period; and (2) the group (Group 2, Experimental Group) that was given the high-fat, high-sugar feed containing Compound A from 4 weeks after the beginning of the test showed a significant decrease in blood glucose level over time in relation to the use of Compound A.

These results clearly indicate that the active ingredient exhibits a blood glucose lowering activity and that it provides an excellent effect for treating diabetes, especially treating type II diabetes.

The invention claimed is:

1. A method for treating diabetes comprising administering to a diabetic patient a therapeutically effective amount of 4-diethoxyphosphinoylmethyl-N-(4-bromo-2-cyanophenyl) benzamide.

2. The method according to claim 1, wherein said diabetic patient has type II diabetes.

3. The method according to claim 1, wherein the diabetes is treated by lowering the blood glucose level of the patient.

4. The method of claim 1, wherein said 4-diethoxyphosphinoylmethyl-N-(4-bromo-2-cyanophenyl)benzamide is administered in the form of a pharmaceutical composition comprising said therapeutically effective amount of 4-diethoxyphosphinoylmethyl-N-(4-bromo-2-cyanophenyl)benzamide and a pharmaceutically acceptable carrier.

* * * * *

UNITED STATES PATENT AND TRADEMARK OFFICE
CERTIFICATE OF CORRECTION

PATENT NO.         : 7,001,896 B2                                Page 1 of 1
APPLICATION NO. : 10/381731
DATED              : February 21, 2006
INVENTOR(S)        : Weidong Yin and Kazuhiko Tsutsumi It is certified that error appears in the above-identified patent and that said Letters Patent is hereby corrected as shown below:

(30) Foreign Application Priority Data
Sep. 29, 2000   PCT/JP00/06741~~(JP)~~............~~2000-06741~~

Signed and Sealed this

Seventeenth Day of October, 2006

JON W. DUDAS
*Director of the United States Patent and Trademark Office*